(12) United States Patent
Pan (10) Patent No.: US 8,277,424 B2
(45) Date of Patent: Oct. 2, 2012

(54) NEEDLE-LESS SYRINGE ADAPTER

(76) Inventor: Hsiu-Feng Pan, Shulin (TW)

(*) Notice: Subject to any disclaimer, the term of this patent is extended or adjusted under 35 U.S.C. 154(b) by 233 days.

(21) Appl. No.: 12/504,780

(22) Filed: Jul. 17, 2009

(65) Prior Publication Data

US 2011/0015566 A1 Jan. 20, 2011

(51) Int. Cl.
*A61M 5/14* (2006.01)
*A61M 5/00* (2006.01)

(52) U.S. Cl. .......................... 604/256; 604/249

(58) Field of Classification Search .................. 604/68, 604/256, 246, 905, 249; 137/843; 251/149.1–149.9
See application file for complete search history.

(56) References Cited

U.S. PATENT DOCUMENTS

| | | | |
|---|---|---|---|
| 5,685,866 A * | 11/1997 | Lopez ........................... | 604/249 |
| 6,050,978 A * | 4/2000 | Orr et al. ...................... | 604/249 |
| 6,189,859 B1 * | 2/2001 | Rohrbough et al. ........ | 251/149.1 |
| 7,470,262 B2 * | 12/2008 | Hiejima et al. ............... | 604/289 |

* cited by examiner

*Primary Examiner* — Christopher D Koharski
*Assistant Examiner* — Jenna Zhang
(74) *Attorney, Agent, or Firm* — Rabin & Berdo, P.C.

(57) ABSTRACT

A needle-less syringe adapter has a tube, a resilient valve, a piercing member and an injection member. The tube has a body has a cavity and an outlet hole. The resilient valve is mounted in the cavity and has a chamber, a top slit and a bottom slit. The piercing conduit is mounted in the chamber, is driven to move when the resilient valve is compressed, selectively extends out through the top and bottom slits and has a through hole defined through the piercing conduit. The injection member is mounted on the tube and is selectively sealed by the resilient valve. The needle-less syringe adapter has excellent hermetical characteristics to prevent air infiltration and backflow of bloody and liquid medicine in a patient's blood vessel.

12 Claims, 8 Drawing Sheets

NEEDLE-LESS SYRINGE ADAPTER

BACKGROUND OF THE INVENTION

1. Field of the Invention

The present invention relates to an adapter, and more particularly to a needle-less syringe adapter that has superior hermetic characteristics to prevent backflow of liquid medicine and remainder of air and liquid medicine therein.

2. Description of Related Art

Needle syringes are common medical implements for injection liquid medicine into patients. However, the needle syringes are dangerous and need recycle procedure that increases the cost of medical treatment.

Therefore, a needle-less syringe has been developed and may be connected to an adapter that is mounted on a cannula. The needle-less syringe has low hazard and may be reused. Therefore, the needle-less syringe lowers the cost of medical treatment.

A conventional adapter for the needle-less syringe has considerable vacant space and undesirable hermetic characteristics so that appreciable amount of liquid medicine and air easily remain in the adapter after an injection procedure is implemented. When the adapter is connected to a needle-less syringe for another injection procedure, the aforementioned remaining liquid medicine and air have been injected into the patient's blood vessel by positive pressure difference between the adapter and the patient's inside. The patient's blood vessel is expanded inadvertently and causes pain. When and injection procedure is finished and the needle-less syringe is disconnected from the adapter, the blood and liquid medicine in the blood vessel flow reversely backwards into the inter space in the adapter due to the negative pressure. Therefore, the inadvertent expansion of vessel during the aforementioned injection procedure makes patients feel pain. The reverse flow of the blood and liquid medicine into the adapter repeatedly mixes new liquid medicine in subsequent injection procedures to lower the curative effect of the liquid medicine and probably cause drug allergy.

To overcome the shortcomings, the present invention provides a needle-less syringe adapter to mitigate or obviate the aforementioned problems.

SUMMARY OF THE INVENTION

The main objective of the invention is to provide a needle-less syringe adapter that has superior hermetic characteristics to prevent backflow of liquid medicine and remainder of air and liquid medicine therein.

A needle-less syringe adapter in accordance with the present invention has a tube, a resilient valve, a piercing member and an injection member. The tube has a body has a cavity and an outlet hole. The resilient valve is mounted in the cavity and has a chamber, a top slit and a bottom slit. The piercing conduit is mounted in the chamber, is driven to move when the resilient valve is compressed, selectively extends out through the top and bottom slits and has a through hole defined through the piercing conduit. The injection member is mounted on the tube and is selectively sealed by the resilient valve.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
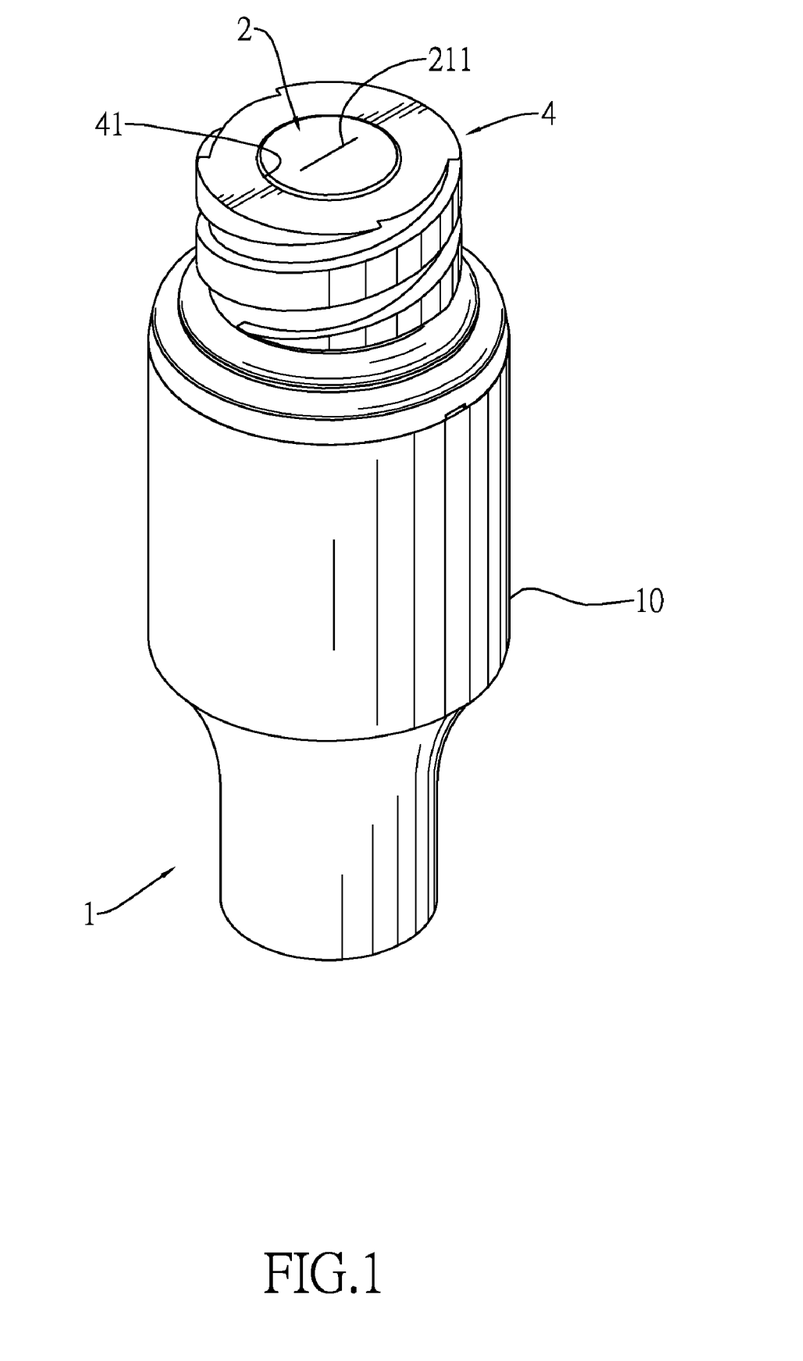
FIG. 1 is a perspective view of a needle-less syringe adapter in accordance with the present invention.
Figure 2:
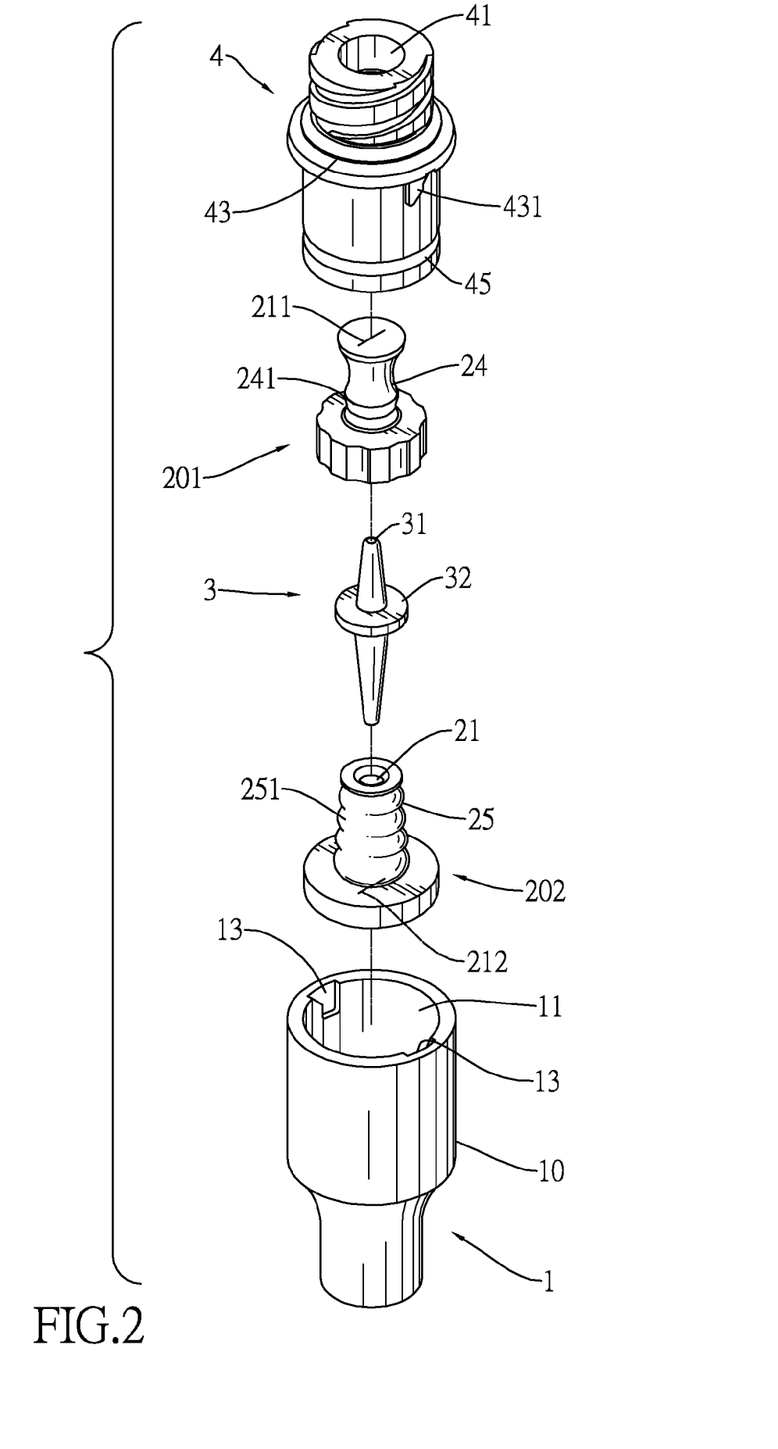
FIG. 2 is an exploded perspective view of the needle-less syringe adapter in FIG. 1.
Figure 3:
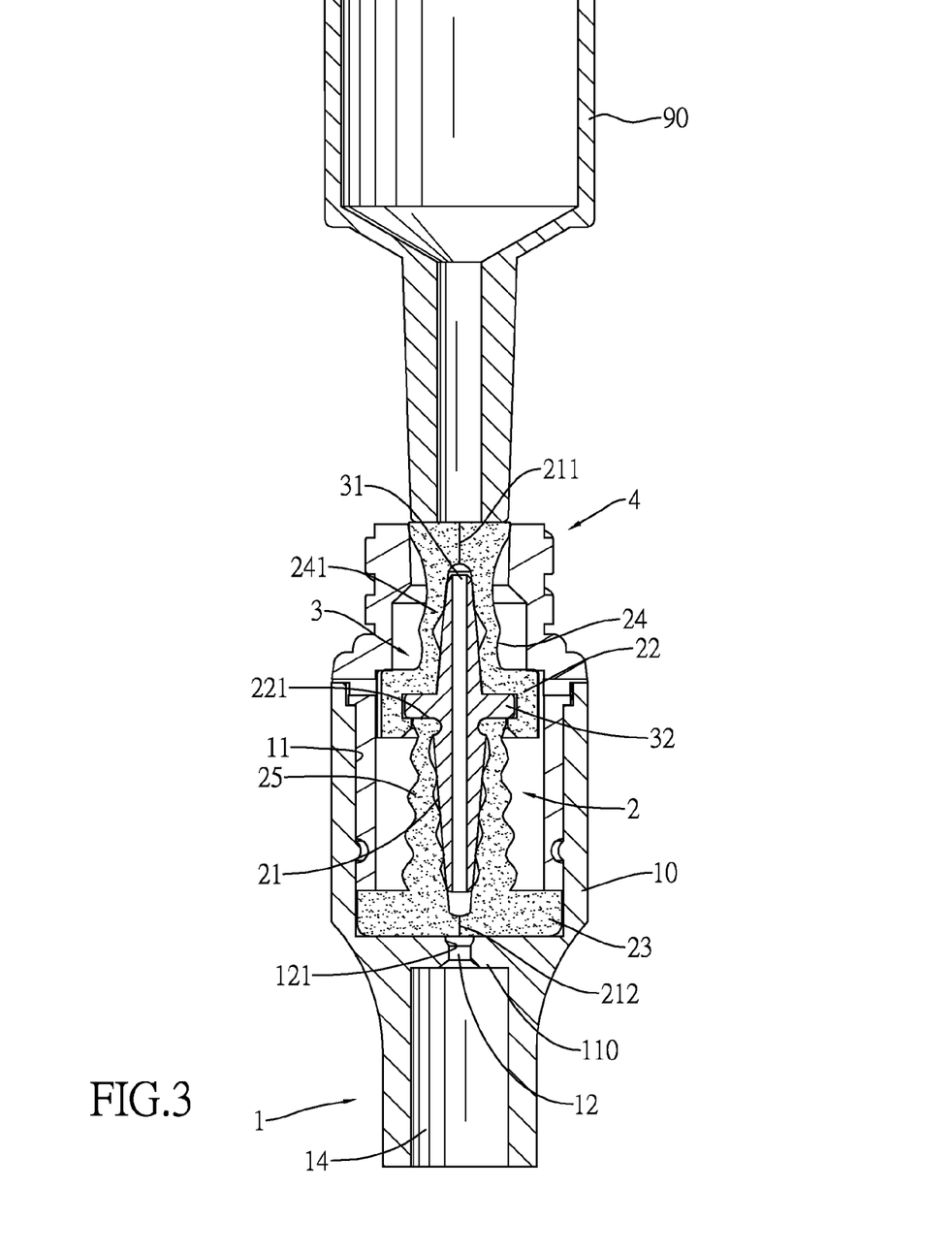
FIG. 3 is an operational cross sectional side view of the needle-less syringe adapter in FIG. 1 connected to a needle-less syringe to implement an injection procedure.

With reference to FIGS. 1 to 3, a first embodiment of a needle-less syringe adapter in accordance with the present invention may be connected to a needle-less syringe (90). The needle-less syringe (90) is mounted on a cannula.

The needle-less syringe adapter in accordance with the present invention comprises a tube (1), a resilient valve (2), a piercing conduit (3) and an injection member (4).

The tube (1) has a body (10) having a top end, a bottom end, a cavity (11), an outlet hole (12) and an outlet channel (14) and may further have at least one positioning notch (13).

The cavity (11) is defined in the top end of the body (10), has an inner surface, a top inlet opening and a bottom partition (110) opposite to the top inlet opening and may further have a rib (111) formed on and protruding from the inner surface of the cavity (11).

The outlet hole (12) is defined through the bottom partition (110) of the cavity (11), communicates with the cavity (11), has an inner surface and may further have a curved concave surface (121) formed on the inner surface adjacent to the cavity (11).

The at least one positioning notch (13) is defined in the inner surface of the cavity (11) adjacent to the top inlet opening of the cavity (11).

The outlet channel (14) is defined in the body (10), is opposite to the cavity (11) relative to the bottom partition (110) and communicates with the outlet hole (12).

The resilient valve (2) is made of resilient material such as rubber and plastic, is hollow and deformable and compressible so that an external force may compress and deform the resilient valve (2). After the removal of the external force, the resilient valve (2) recovers to the original shape thereof. The resilient valve (2) is mounted in the cavity (11) of the tube (1) and has a top, a bottom and a chamber (21) and may further have a guide (22).

The bottom of the resilient valve (2) is mounted on the bottom partition (110) of the cavity (11) and may have a pad (23) formed on the bottom.

The chamber (21) is defined in the resilient valve (2) and has a top slit (211) and a bottom slit (212). The top slit (211) is defined through the top of the resilient valve (2) and selectively closes to seal the chamber (21) or opens to communicate with the chamber (21). A default configuration of the top slit (211) is closed when no external force is applied thereto. The bottom slit (212) is defined through the bottom of the resilient valve (2) and selectively closes to seal the chamber (21) or opens to communicate with the chamber (21). A default configuration of the bottom slit (212) is closed when no external force is applied thereto.

The guide (22) is formed on and protrudes radially from the resilient valve (2) and slidably contacts the inner surface of the cavity (11) of the tube (1) so that the guide (22) is capable of sliding longitudinally along the inner surface of the cavity (11). The guide (22) further has a mounting element. The mounting element is formed in the chamber (21) and may be a mounting recess (221).

In a preferred embodiment, the resilient valve (2) are assembled from a top half (201) and a bottom half (202).

The top half (201) is substantially conical, is deformable and has a crown-like top and a top deforming section (24) being compressible and having at least one wrinkled portion (241). The at least one wrinkled portion (241) is formed radially on the top deforming section (24) to facilitate the deformation of the top half (24).

The bottom half (202) is substantially conical, may be thicker than the top half (201), is deformable and has a crown-like bottom and a bottom deforming section (25) being compressible and having at least one wrinkled portion (251). The at least one wrinkled portion (251) is formed radially on bottom deforming section (25) to facilitate the deformation of the bottom half (25).

The piercing conduit (3) is shuttle-like, is tapered from an intermediate respectively toward top and bottom ends thereof so that an outer surface thereof has slope. The top end of the piercing conduit (3) selectively extends out through the top slit (211) of the resilient valve (2). The bottom end of the piercing conduit (3) selectively extends out through the bottom slit (212) of the resilient valve (2) and may have a curved convex surface corresponding to and selectively contacting the curved concave surface of the outlet hole (12) of the tube (1) hermetically. The piercing conduit (3) has a through hole (31) and may further have a mounting member. The through hole (31) is defined longitudinally through the piercing conduit (3) from the top end to the bottom end, selectively communicates with ambient atmosphere and selectively communicates with the outlet hole (12). The mounting member is formed radially on the piercing conduit (3) and is mounted on the mounting element of the guide (22) of the resilient valve (2) so that the piercing member (3) is driven to move upward and down synchronously with the guide (22). The mounting member may be a mounting protrusion (32) mounted securely in the mounting recess (221) of the resilient valve (2).

The injection member (4) is mounted on the top end of the body (10) of the tube (1) and has a top end, a bottom end, an internal space (41), a cap (43) and a groove (45).

The bottom end of the injection member (4) may hermetically abut the pad (23) of the resilient valve (2).

The internal space (41) is defined in the injection member (4), accommodates the resilient valve (2) and has a top injection opening and a bottom opening. The top injection opening is selectively closed by the top of the resilient valve (2). The top injection opening is sealed when no external force is applied to the resilient valve (2).

The cap (43) is formed on and protrudes radially from the injection member (4), is mounted on the top end of the body (10) of the tube (1) and may have at least one positioning projection (431) engaged respectively with the at least one positioning notch (13) of the tube (1).

The groove (45) is defined radially in the injection member (4) and is engaged with the rib (111) in the cavity (11) of the tube (1).

With reference to FIG. 3, when the needle-less syringe (90) is not inserted into the injection member (4), the crown-like top of the top half (24) of the resilient valve (2) seals the top injection opening of the internal space (41). The top and bottom slits (211, 212) of the resilient valve (2) are both closed.

Figure 4:
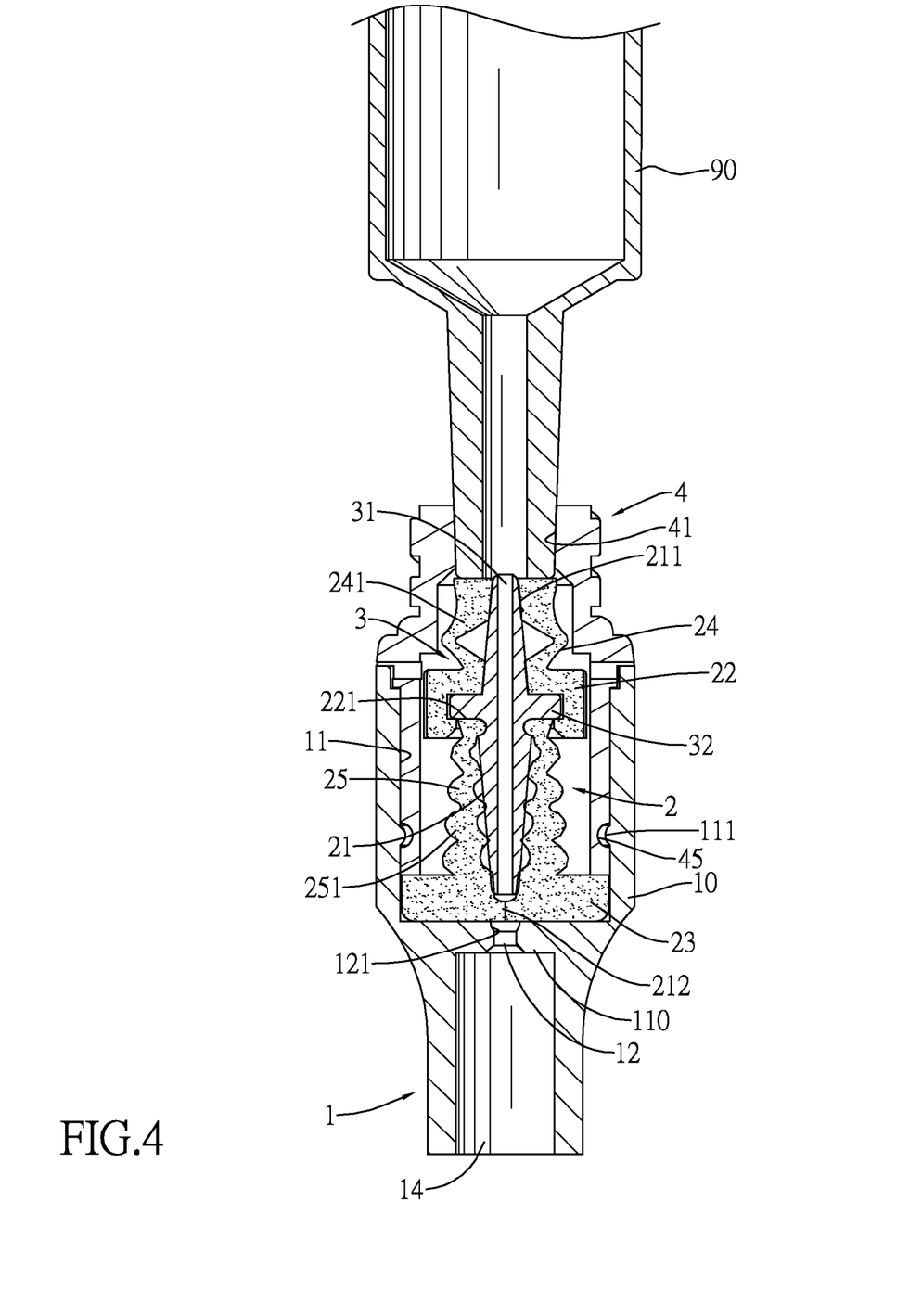
FIG. 4 is an operational cross sectional side view of the needle-less syringe adapter in FIG. 3 with the needle-less syringe moving down and compressing the resilient valve halfway so that an outside opening of the resilient valve is opened.

With further reference to FIG. 4, when the needle-less syringe (90) is inserted into the top injection opening of the internal space (41) of the injection member (4) and compresses the top of the resilient valve (2), the top slit (211) of the resilient valve (2) is pierced and opened by the piercing conduit (3) and the through hole (31) of the piercing conduit (3) communicates with the needle-less syringe (90).

Figure 5:
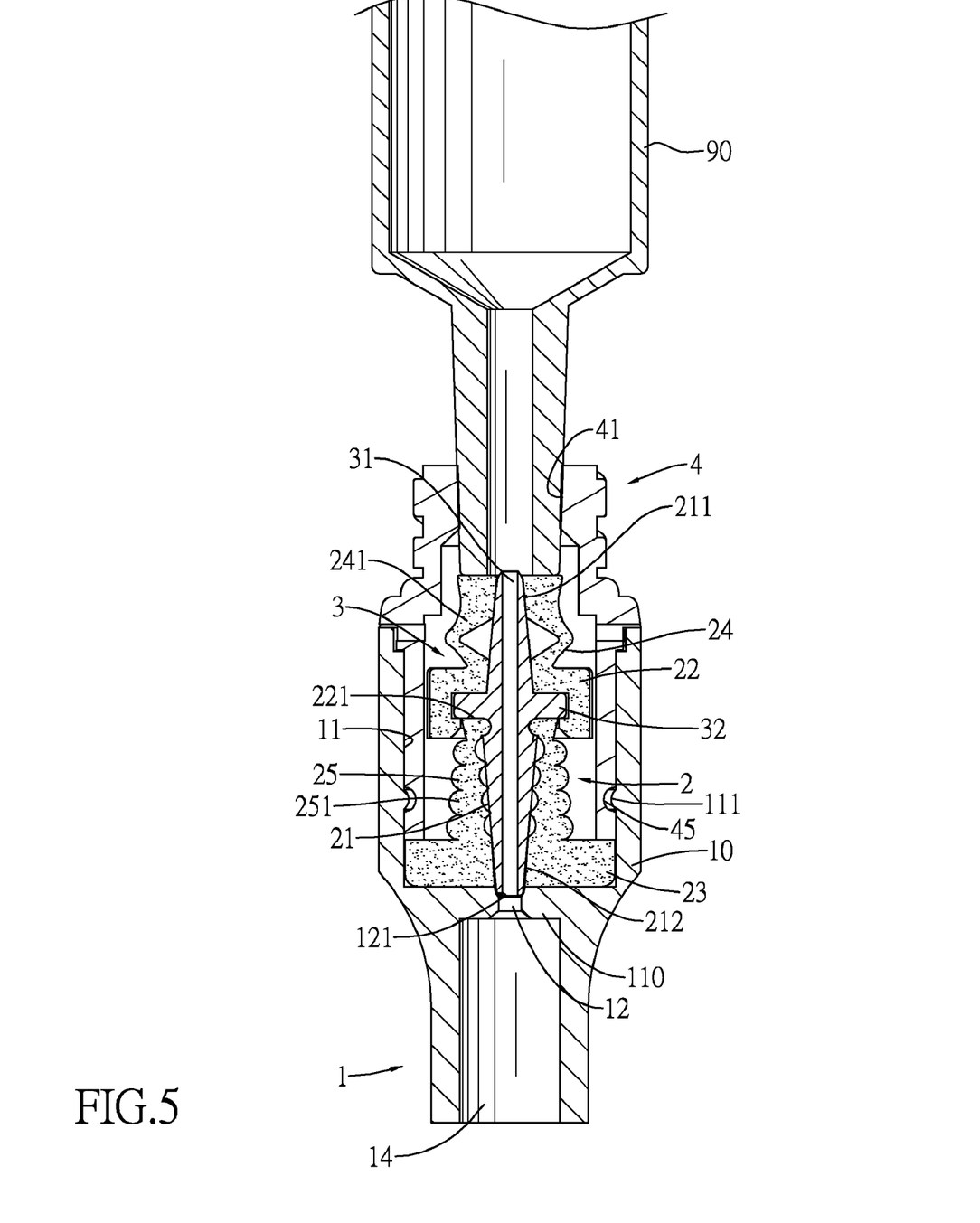
FIG. 5 is a an operational cross section side view of the needle-less syringe adapter in FIG. 4 with the needle-less syringe completely moving down and compressing the resilient valve to further open the inside opening thereof.

With further reference to FIG. 5, the needle-less syringe (90) is further inserted down into the top injection opening of the internal space (41) of the injection member (4). The guide (22) of the resilient valve (2) and the piercing conduit (3) move down synchronously so that the piercing conduit (3) pierces and opens the bottom slit (212) of the resilient valve (2). The needle-less syringe (90), through hole (31) of the piercing conduit (3) and outlet hole (12) of the tube (1) communicate with one another so that liquid medicine flows into the outlet channel (14).

When the injection procedure is finished and the needle-less syringe (90) is removed, the top and bottom slits (211, 212) recover to close. The air in the internal space (41) of the injection member (4) and the cavity (11) of the tube (1) is discharged through gaps between the cap (43) and the top end of the body (10).

Figure 6:
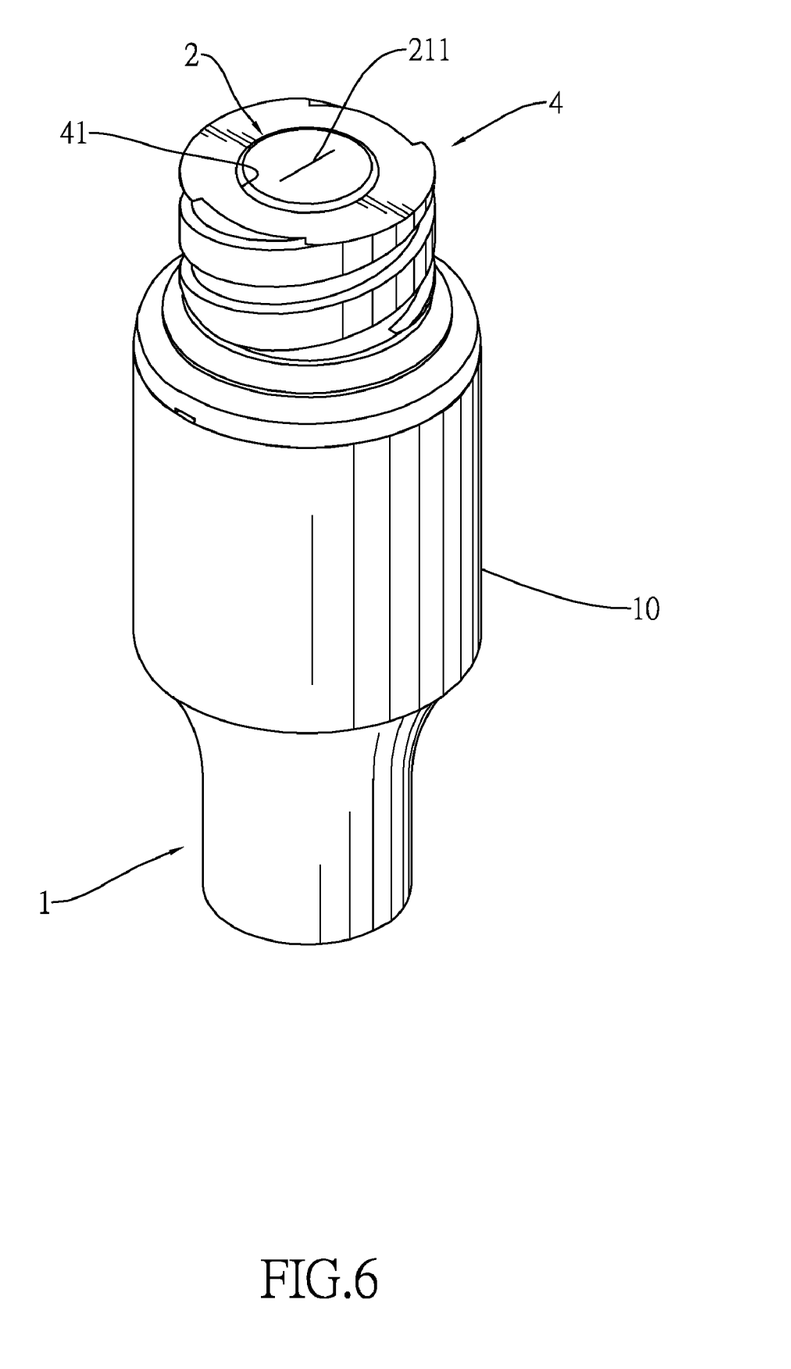
FIG. 6 is a perspective view of a second embodiment of a needle-less syringe adapter in accordance with the present invention.
Figure 7:
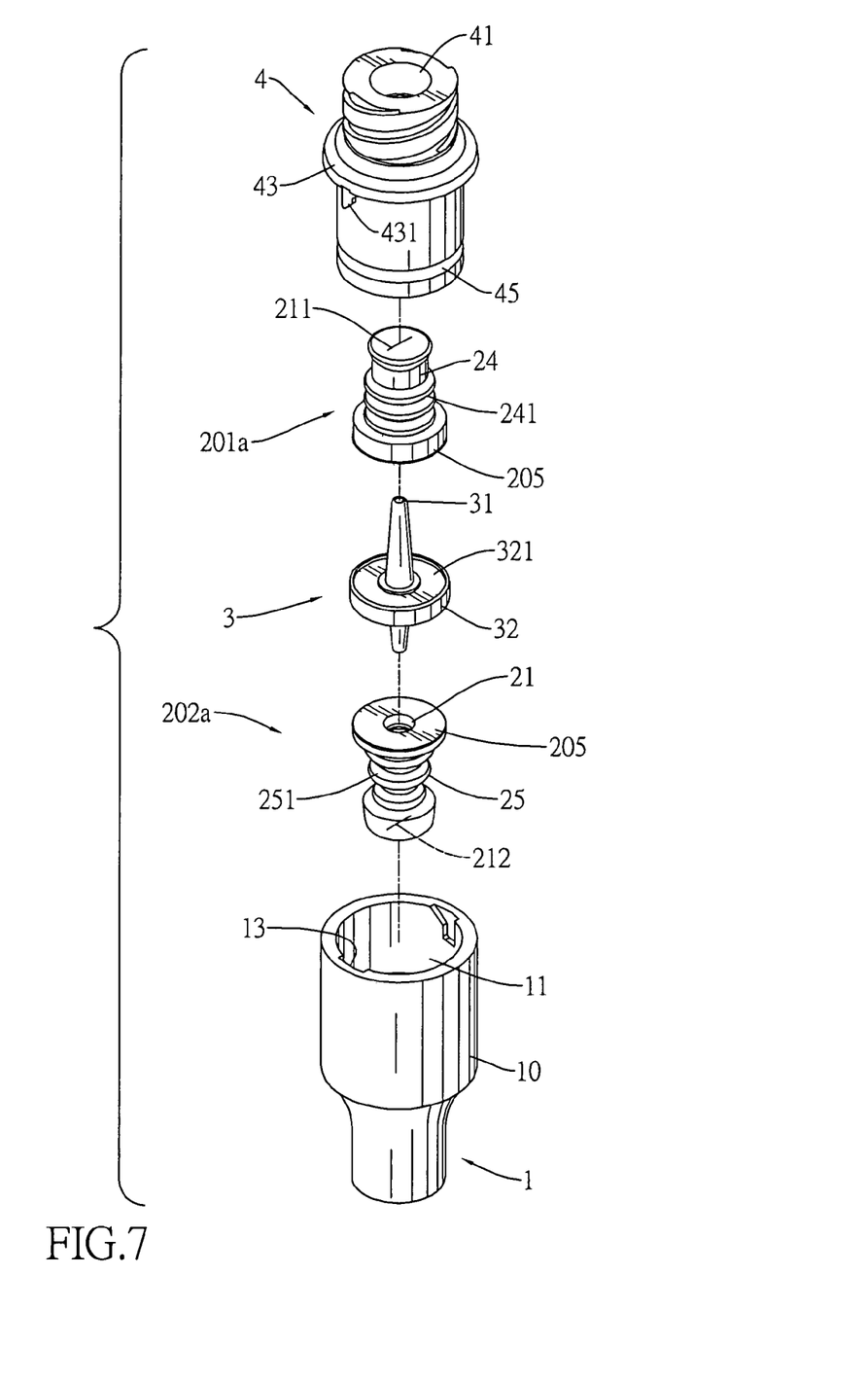
FIG. 7 is an exploded perspective view of the needle-less syringe adapter in FIG. 6.
Figure 8:
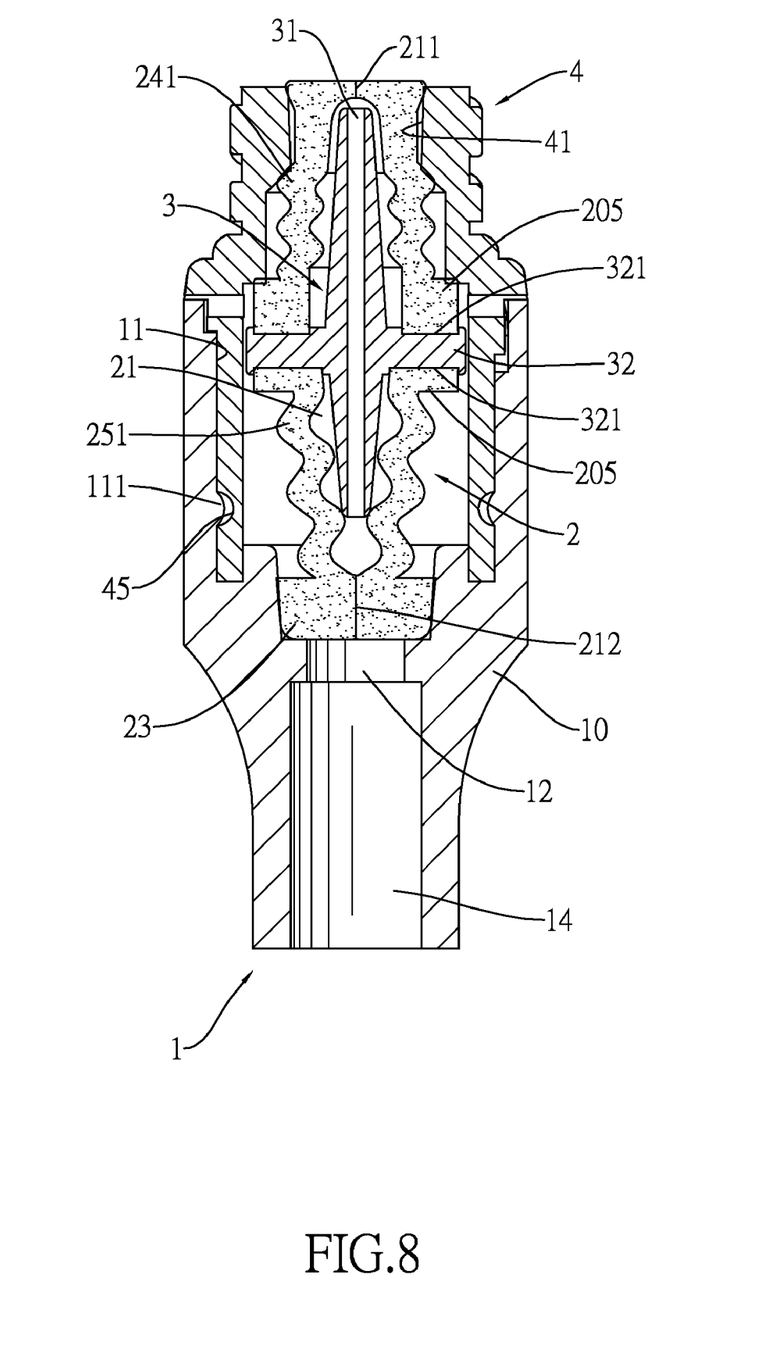
FIG. 8 is a cross sectional side view of the needle-less syringe adapter in FIG. 7.

With further reference to FIGS. 6 to 8, a second embodiment of the needle-less syringe adapter in accordance with the present invention is similar to the first embodiment. However, each of the top and bottom halves (201a, 202a) has a mounting flange (205) formed radially thereon. The mounting protrusion (32) of the piercing conduit (3) has two opposite mounting slots (321) defined in the mounting protrusion (32) and engaged respectively with the mounting flanges (205).

The present invention has following advantages.

1. Before the connection of the needle-less syringe (90), the resilient valve (2) hermetically closes the top and bottom slits (211, 212) to prevent ambient air or liquid medicine and blood of a patient's blood vessel from flowing into the resilient valve (2). After the removal of the needle-less syringe (90), the compressed resilient valve (2) recovers fast along the slope of the piercing conduit (3) to immediately close the top and bottom slits (211, 212) to prevent any reverse flow of the air, liquid medicine and blood. Therefore, the needle-less syringe adapter reduces the patient's pain.

2. The structure of the needle-less syringe adapter maximally reduces the vacant space thereof so air, liquid medicine and bloody seldom remain therein. Thus the positive and negative pressures during an injection procedure efficiently decrease.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A needle-less syringe adapter, comprising:
a tube having a body having
   a top end;
   a bottom end;
   a cavity defined in the top end and having an inner surface, a top inlet opening and a bottom partition opposite to the top inlet opening;
   an outlet hole defined through the bottom partition of the cavity, communicating with the cavity and having an inner surface; and
   an outlet channel defined in the body and communicating with the outlet hole;
a resilient valve mounted in the cavity of the tube and having a top, a bottom and a chamber defined in the resilient valve and having
   a top slit defined through the top of the resilient valve and selectively closing to seal the chamber or opening to communicate with the chamber, wherein a default configuration of the top slit is closed; and
   a bottom slit defined through the bottom of the resilient valve and selectively closing to seal the chamber or opening to communicate with the chamber, wherein a default configuration of the bottom slit is closed;
a piercing conduit formed as a unitary piece and tapered from an intermediate respectively toward top and bottom ends thereof so that an outer surface of the piercing conduit has slope, a top end of the piercing conduit selectively extending out through the top slit, a bottom end of the piercing conduit selectively extending out through the bottom slit, wherein
   the piercing conduit has a through hole defined longitudinally through the piercing conduit from the top end to the bottom end and selectively communicating with the outlet hole and
   the through hole has a top opening defined on the top end and facing upward instead of facing radially inward, and a bottom opening defined on the bottom end and facing downward instead of facing radially inward, wherein the top opening is entirely revealed out of the resilient valve when the top end of the piercing conduit extends out through the top slit, and the bottom opening is entirely revealed out of the resilient valve when the bottom end of the piercing conduit extends out through the bottom slit; and
an injection member mounted on the top end of the body of the tube and having a top end, a bottom end and an internal space defined therein,
wherein when the needle-less syringe adapter is not used, the top and bottom slits of the resilient valve are closed to seal the injection member and the outlet hole of the tube and the resilient valve encloses the piercing conduit, and
a ventilation hole is defined between the tube and injection member so that air in the internal space of the injection member and the cavity of the tube is discharged through the ventilation hole.

2. The needle-less syringe adapter as claimed in claim 1, wherein the internal space of the injection member accommodates the resilient valve and defines a top injection opening selectively closed by the top of the resilient valve, and
a bottom opening.

3. The needle-less syringe adapter as claimed in claim 2, wherein
the outlet hole of the bottom partition of the tube further has a curved concave surface formed on the inner surface adjacent to the cavity ; and
the bottom end of the piercing conduit has a curved convex surface corresponding to and selectively contacting the curved concave surface of the outlet hole of the tube hermetically.

4. The needle-less syringe adapter as claimed in claim 2, wherein the resilient valve further has a guide formed on and protruding radially from the resilient valve, the guide slidably contacting the inner surface of the cavity of the tube and driving the piercing conduit to move synchronously.

5. The needle-less syringe adapter as claimed in claim 4, wherein
the guide of the resilient valve further has a mounting element formed in the chamber; and
the piercing conduit further has a mounting member formed on the piercing conduit and mounted on the mounting element of the guide of the resilient valve.

6. The needle-less syringe adapter as claimed in claim 5, wherein the mounting element is a mounting recess and the mounting member is a mounting protrusion mounted securely in the mounting recess.

7. The needle-less syringe adapter as claimed in claim 1, wherein the resilient valve has a top deforming section being compressible and having at least one wrinkled portion formed radially on the top deforming section.

8. The needle-less syringe adapter as claimed in claim 7, wherein the resilient valve further has a bottom deforming section being compressible and having at least one wrinkled portion formed radially on the bottom deforming section.

9. The needle-less syringe adapter as claimed in claim 1, wherein
the resilient valve further has a pad formed on the bottom of the resilient valve; and
the bottom end of the injection member abuts the pad of the resilient valve.

10. The needle-less syringe adapter as claimed in claim 1, wherein
the cavity of the tube further has a rib formed on and protruding from the inner surface of the cavity; and
the injection member further has a groove defined radially in the injection member and engaged with the rib.

11. The needle-less syringe adapter as claimed in claim 1, wherein
the body of the tube further has at least one positioning notch defined in the inner surface of the cavity adjacent to the top inlet opening; and
the injection member further has a cap formed on and protruding radially from the injection member, mounted on the top end of the body of the tube and having at least one positioning projection engaged respectively with the at least one positioning notch of the tube.

12. A needle-less syringe adapter, comprising:
a tube having a body having
   a top end;
   a bottom end;
   a cavity defined in the top end and having an inner surface, a top inlet opening and a bottom partition opposite to the top inlet opening;
   an outlet hole defined through the bottom partition of the cavity, communicating with the cavity and having an inner surface; and
   an outlet channel defined in the body and communicating with the outlet hole;
a resilient valve mounted in the cavity of the tube and having a top, a bottom and a chamber defined in the resilient valve and having
   a top slit defined through the top of the resilient valve and selectively closing to seal the chamber or opening to communicate with the chamber, wherein a default configuration of the top slit is closed; and a bottom slit defined through the bottom of the resilient valve and selectively closing to seal the chamber or opening to communicate with the chamber, wherein a default configuration of the bottom slit is closed;

a piercing conduit formed as a unitary one piece and tapered from an intermediate respectively toward top and bottom ends thereof so that an outer surface of the piercing conduit has slope, a top end of the piercing conduit selectively extending out through the top slit, a bottom end of the piercing conduit selectively extending out through the bottom slit, wherein the piercing conduit has a through hole defined longitudinally through the piercing conduit from the top end to the bottom end and selectively communicating with the outlet hole and the through hole has a top opening defined on the top end and facing upward instead of facing radially inward, and a bottom opening defined on the bottom end and facing downward instead of facing radially inward, wherein the top opening is entirely revealed out of the resilient valve when the top end of the piercing conduit extends out through the top slit, and the bottom opening is entirely revealed out of the resilient valve when the bottom end of the piercing conduit extends out through the bottom slit; and an injection member mounted on the top end of the body of the tube and having a top end, a bottom end and an internal space defined therein;

wherein when the needle-less syringe adapter is not used, the top and bottom slits of the resilient valve are closed to seal the injection member and the outlet hole of the tube and the resilient valve encloses the piercing conduit, and a ventilation hole is defined between the tube and injection member so that air in the internal space of the injection member and the cavity of the tube is discharged through the ventilation hole; and wherein the resilient valve is assembled from a top half and a bottom half, each of the top and bottom halves has a mounting flange formed radially on each of the top and bottom halves, and the piercing conduit has a mounting protrusion formed radially on the piercing conduit and having two opposite mounting slots defined in the mounting protrusion and engaged respectively with the mounting flanges.

* * * * *